United States Patent
Green

(10) Patent No.: US 7,908,121 B2
(45) Date of Patent: Mar. 15, 2011

(54) DETERMINATION OF TIME ZERO FROM A CHARGED PARTICLE DETECTOR

(75) Inventor: Jesse Andrew Green, Los Alamos, NM (US)

(73) Assignee: Los Alamos National Security, LLC, Los Alamos, NM (US)

(*) Notice: Subject to any disclaimer, the term of this patent is extended or adjusted under 35 U.S.C. 154(b) by 374 days.

(21) Appl. No.: 11/977,313

(22) Filed: Oct. 24, 2007

(65) Prior Publication Data

US 2008/0228418 A1 Sep. 18, 2008

Related U.S. Application Data

(60) Provisional application No. 60/855,064, filed on Oct. 27, 2006.

(51) Int. Cl.
| | |
|---|---|
| G01T 5/00 | (2006.01) |
| G01N 23/00 | (2006.01) |
| G01D 21/00 | (2006.01) |
| G21K 1/00 | (2006.01) |
| G21K 1/10 | (2006.01) |
| G06F 19/00 | (2006.01) |

(52) U.S. Cl. ............ 702/189; 250/306; 250/580; 702/1; 702/30

(58) Field of Classification Search .................. 250/281, 250/306, 336.1, 358.1, 359.1, 360.1, 374, 250/389, 390.01, 391, 392, 394, 580; 324/71.1, 324/71.3, 71.4; 702/1, 22, 26, 29, 30, 85, 702/87, 127, 128, 187, 189
See application file for complete search history.

(56) References Cited

U.S. PATENT DOCUMENTS

| | | | | |
|---|---|---|---|---|
| 3,891,851 | A * | 6/1975 | Fletcher et al. | 250/385.1 |
| 7,049,603 | B2 * | 5/2006 | Martoff | 250/390.02 |
| 7,157,719 | B2 * | 1/2007 | Martoff | 250/390.02 |
| 7,470,905 | B1 * | 12/2008 | Goldberg et al. | 250/358.1 |
| 7,633,062 | B2 * | 12/2009 | Morris et al. | 250/308 |
| 2006/0017000 | A1 * | 1/2006 | Martoff | 250/390.02 |
| 2006/0261283 | A1 * | 11/2006 | Martoff | 250/390.02 |
| 2007/0102648 | A1 * | 5/2007 | Shpantzer et al. | 250/394 |
| 2008/0191133 | A1 * | 8/2008 | Morris et al. | 250/307 |
| 2008/0265156 | A1 * | 10/2008 | Morris et al. | 250/305 |

(Continued)

OTHER PUBLICATIONS

Borozdin, Konstantin et al., "Cosmic-Ray Muon Tomography and Its Application to the Detection of High-Z Materials", Proceedings of the 46th Annual Meeting, Institute of Nuclear Materials Management, 2005, pp. 1-8.

(Continued)

Primary Examiner — Edward R Cosimano
(74) Attorney, Agent, or Firm — Matthew F. Lambrinos; Kermit D. Lopez; Luis M. Ortiz

(57) ABSTRACT

A method, system and computer program is used to determine a linear track having a good fit to a most likely or expected path of charged particle passing through a charged particle detector having a plurality of drift cells. Hit signals from the charged particle detector are associated with a particular charged particle track. An initial estimate of time zero is made from these hit signals and linear tracks are then fit to drift radii for each particular time-zero estimate. The linear track having the best fit is then searched and selected and errors in fit and tracking parameters computed. The use of large and expensive fast detectors needed to time zero in the charged particle detectors can be avoided by adopting this method and system.

24 Claims, 10 Drawing Sheets

U.S. PATENT DOCUMENTS

2010/0032564 A1* 2/2010 Morris et al. .................. 250/307

OTHER PUBLICATIONS

Van Eijik, Carl W.E., "Neutrons PSD's for the Next Generation of Spallation Neutron Sources" Nuclear Instruments and Methods in Physics Research A, 2002, vol. 477, pp. 383-390.

Hengartner, Nicolas et al., Information Extraction for Muon Radiography, Nuclear Science Symposium Conference Record, 2005 IEEE, vol. 1, Oct. 23-29, 2005, pp. 11-15.

Fessler, Jeffrey A. "Statistical Methods for Image Reconstruction" (annotated slides for attendees of the NSS-MIC short Course), Oct. 24, 2004.

Schultz, L. J. et al., "Image Reconstruction and Material Z Discrimination via Cosmic Ray Muon Radiography", Nuclear Instruments and Methods in Physics Research A, 2004, vol. 519, pp. 687-694.

Jenneson, P.M. "Large Vessel Imaging Using Cosmic-ray Muons", Nuclear Instruments and Methods in Physics Research A, 2004, vol. 525, pp. 346-351.

PCT—Notification of Transmittal of the International Search Report and the Written Opinion of the International Searching Authority, or the Declaration, Date of Mailing, Jan. 23, 2009.

A Terrorist Threat—The Movement of Black Market Nuclear Materials into the United States; Gene R. Kelley, Nov. 17, 2001; .wagingpeace.org/articles/2001/11/17_kelley_terrorist-threat.htm.

Radiographic Imaging with Cosmic-Ray Muons; K.N. Borozdin, G.E. Hogan, C. Morris, W.C. Priedhorsky, A. Saunders, L.J. Schultz, M.E. Teasdale; Los Alamos National Laboratory; vol. 422, Mar. 20, 2003, .nature.com/nature.

Detection of High-Z Objects Using Multiple Scattering of Cosmic Ray Muons; W.C. Priedhorsky, K.N. Borozdin, G.E. Hogan, C. Morris, A. Saunders, L.J. Schultz, M.E. Teasdale; Review of Scientific Instruments, vol. 74, No. 10, Oct. 2003.

Cosmic Ray Muon Radiography; Larry J. Schultz; Dissertation for Ph.D. Electrical and Computer Engineering, Portland State University 2003.

Image Reconstruction and Material Z Discrimination Via Cosmic Ray Muon Radiography; L.J. Schultz, K.N. Borozdin, J.J. Gomez, G.E. Hogan, J.A. McGill, C.L. Morris, W.C. Priedhorsky, A. Saunders, M.E. Teasdale; NIM Submission Draft—Jun. 30, 2003.

Unger, M. "Detection of Cosmic Muons with Scintillating Tiles on Top of the L3 Detector", Masters Thesis of Institute for Physics, Faculty of Mathematics and Natural Sciences I, Humboldt-Universitat zu Berlin, 1999.

* cited by examiner

DETERMINATION OF TIME ZERO FROM A CHARGED PARTICLE DETECTOR

CROSS-REFERENCE TO PROVISIONAL APPLICATION

This application claims priority under 35 U.S.C §119(e) to expired U.S. provisional patent application No. 60/855,064, entitled "Systems, Methods and Apparatus for Particle Detection and Analysis and Field Deployment of the Same", which was filed Oct. 27, 2006, the disclosure of which is incorporated herein by reference.

STATEMENT REGARDING FEDERAL RIGHTS

This invention was made with Government support under Contract Number DE-AC52-06NA25396 awarded by the United States Department of Energy. The Government has certain rights in the invention.

TECHNICAL FIELD

Embodiments relate to fields of particle detection, analysis, control and, more particularly but not exclusively, to methods and systems for analyzing data from a charged particle detection system having a plurality of drift tubes, chambers, or other particle detection devices and for reconstructing the trajectory of a charged particle, such as a cosmic ray-produced muon, passing through the charged particle detection system.

BACKGROUND OF THE INVENTION

Charged particle detection systems can be used to detect charged particles passing through a volume.

Cosmic ray charged particle detectors detect muons or other cosmic ray-produced charged particles. Natural background cosmic ray-produced charged particles, such as muons, are generated by cosmic rays and are highly penetrating. Primary cosmic rays, which are mostly high-energy protons, interact in the upper atmosphere, producing many particles including pions which decay into muons (lifetime=2.2 microseconds). Muons interact only through the Coulomb and weak force. Muons arrive at the Earth's surface at a rate of about 1/cm$^2$/minute/steradian in a broad distribution (about 1 steradian) of generally-downward directions.

A system and method for tracking the detected cosmic ray or other charged particles is needed. It is believed that the method and system of the illustrative embodiments provides an effective way of tracking the detected cosmic ray—produced muon or other charged particles.

SUMMARY

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

The aforementioned aspects of the invention and other objectives and advantages can now be achieved as described herein.

According to one aspect, a detection system is described for reconstructing the trajectory of a charged particles passing through the object volume. This system includes a first set of position sensitive detectors located on a first side of an object volume to measure positions and angles of incident charged particles towards the object volume; a second set of position sensitive detectors located on a second side of the object volume opposite to the first side to measure positions and angles of outgoing charged particles exiting the object volume; and a signal processing unit to receive data of measured signals from the first set of position sensitive detectors and measured signals from the second set of position sensitive detectors. The signal processing unit processes the received data to construct the trajectory of a charged particle.

According to another aspect, a method for reconstructing the trajectory of a charged particle passing through a charged particle detector having a plurality of drift cells comprises (a) obtaining hit signals representing identifiers of drift cells hit by charged particles and corresponding hit times; (b) grouping in-time drift cell hits identified as being associated with a track of a particular charged particle passing through the detector; (c) initially estimating time zero for the particular charged particle; (d) determining drift radii based on estimates of time zero, drift time conversion data and the time of the hit; (e) fitting linear tracks to drift radii corresponding to a particular time-zero; and (f) searching and selecting a time-zero value associated with the best of the track fits performed for particular charged particle and computing error in time-zero and tracking parameters.

Reconstructing the track based on the time zero fit provides a reconstructed linear trajectory of the charged particle passing through the charged particle detector without having to use fast detectors (such as photomultiplier tubes with scintillator paddles) or some other fast detector (which actually detects the passage of the muon through the apparatus to the nearest few nanoseconds) to provide time-zero. The charged particles can be cosmic ray-produced charged particles, such as cosmic ray muons, charged particles produced by another source such as an accelerator.

The method can include detecting with drift cells the charged particle passing through the detector preparatory to obtaining the hit signals.

Obtaining hit signals representing identifiers of drift cells hit by charged particles and corresponding hit times can comprise reading times of the drift cell hits; reading corresponding drift cell channel numbers; and optionally subtracting times to account for propagation delay and/or approximate time of flight of particular charged particle.

Initially estimating time zero for the particular charged particle can comprise initially estimating time zero for the particular charged particle from the grouped hits. Grouping in-time drift cell hits identified as being associated with a track of a particular charged particle passing through the detector can comprise grouping hit times within a predetermined time window associated with the track; and including only those hits most likely to be part of the particular charged particle track.

Obtaining hit signals representing identifiers of drift cells hit by charged particles and corresponding hit times can comprise obtaining hit signals from a first set of drift cells positioned on a side of an object volume to measure the position of incoming charged particles entering the object volume; the first set of drift cells having drift cells configured in a first component direction and in a second component direction; and obtaining hit signals from a second set of drift cells positioned on a side of an object volume to measure the position of outgoing charged particles exiting the object volume; the second set of drift cells having drift cells configured in a first component direction and in a second component direction.

The method can include determining if the grouped hits include at least three hit signals from the first set drift cells positioned in a first component direction and at least three hit signals from the first set drift cells positioned in a second component direction; and determining if the grouped hits include at least three hit signals from the second set drift cells positioned in a first component direction and at least three hit signals from the second set drift cells positioned in a second component direction.

The method can further comprise obtaining hit signals representing identifiers of drift cells hit by charged particles and corresponding hit times for the next track event in response to determining the grouped hit signals do not include the at least three hit signals from the appropriate drift cells of each first and second drift cell sets.

Initially estimating time zero for the particular charged particle can comprise determining the metric based upon hit times of the grouped hits; and subtracting a constant from the metric hit time. Determining the metric hit time can comprise determining the median hit time of the grouped hits.

Fitting linear tracks to drift radii corresponding to a particular time-zero can include fitting the tracks to drift radii using linear regression formulas or an iterative fit in order to minimizes the aggregate distance from a track to anode wire of the drift cell.

Determining drift radii based on estimates of time zero, drift time conversion data and the time of the hit can comprise subtracting each hit time of the grouped hits from the initial estimate of time zero to determine each drift time of each hit; and converting the drift times to radii based on predetermined experimental/theoretical drift time to drift distance data stored in a database.

Fitting linear tracks to drift radii corresponding to a particular time-zero can include fitting linear tracks of charged particles passing through the first set and second set of drift cells, respectively, using obtained drift radii; and wherein searching and selecting a time-zero value associated with the best of the track fits performed for particular charged particle and computing error in time-zero and tracking parameters can comprise estimating each next time zero from track fits for first and second drift cell sets; and for each next time zero, determining drift radii based on estimates of time zero, drift time conversion data and the time of the hit, and fitting linear tracks to drift radii corresponding to time-zero until a substantially linear track having a best fit to most likely or expected path of charged particle passing through detector is obtained.

Fitting linear tracks to drift radii corresponding to a particular time-zero can include fitting linear tracks of charged particles passing through the first set and second set of drift cells, respectively, to obtained drift radii; and wherein searching and selecting a time-zero value associated with the best of the track fits performed for particular charged particle and computing error in time-zero and tracking parameters can comprise determining a minimum value of chi-square based on the track fits for the first and second sets of drift cells and the drift radii; adding together chi-squares for fitted tracks to determine total chi-square; storing chi-square value for each estimate of value of time-zero; performing a search to determine time-zero corresponding to the lowest estimated value of chi-square; and determining a parabolic fit to at least three lowest points to determine error of time-zero selection; and determine linear track using correct time-zero selection.

According to yet another aspect, a system for reconstructing the trajectory of a charged particle passing through a detector having a plurality of drift cells is adapted and arranged to (a) obtain hit signals representing identifiers of drift cells hit by charged particles and corresponding hit times; (b) group in-time drift cell hits identified as being associated with a track of a particular charged particle passing through the detector; (c) initially estimate time zero for the particular charged particle; (d) determine drift radii based on estimates of time zero, drift time conversion data and time of the hit; (e) fit linear tracks to drift radii corresponding to a particular time-zero; and (f) search and select a time-zero value associated with the best of the track fits performed for particular charged particle and compute error in time-zero and tracking parameters. The charged particle can comprise a cosmic ray-produced charged particle, such as a muon, or charged particle produced by another source.

The controller can obtain hit signals from a charged particle detector operably linked to the controller. The charged particle detector can have having a first set of drift cells positioned on one side of an object receiving volume to measure positions of incoming charged particles entering the object volume, and having a second set of drift cells positioned on another side of the object volume to measure positions of outgoing charged particles exiting the object volume;

The controller can be adapted and arranged to: read times of the drift cell hits; read corresponding drift cell channel numbers; and optionally subtracting times to account for propagation delay and/or approximate time of flight of particular charged particle.

The controller can be adapted and arranged to group hit times within a predetermined time window associated with the track; and include only those hits most likely to be part of the particular charged particle track.

The controller can be adapted and arranged to determine the metric based upon hit times of the grouped hits; and subtract a constant from the metric hit time in order to provide an initially estimate time zero.

The controller can be adapted and arranged to subtract each hit time of the grouped hits from the initial estimate of time zero to determine each drift time of each hit; and convert the drift times to radii based on predetermined experimental/theoretical drift time to drift distance data stored in a database.

The controller can be adapted and arranged to: fit linear tracks of charged particles passing the first set of drift cells and the second set of cells, respectively, to obtained drift radii; determine a minimum value of chi-square based on the track fits for the first and second sets of drift cells and the drift radii; add together chi-squares for fitted tracks to determine total chi-square; store chi-square value for each estimate of value of time-zero; perform a search to determine time-zero corresponding to the lowest estimated value of chi-square; determine a parabolic fit to at least three lowest points to determine error of time-zero selection; and determine linear track using correct time-zero selection.

According to yet another aspect, a computer program product comprises: a computer-usable data carrier storing instructions that, when executed by a computer, cause the computer to perform a method for reconstructing the trajectory of a charged particle passing through a detector having a plurality of drift cells, the method comprising: (a) obtaining hit signals representing identifiers of drift cells hit by charged particles and corresponding hit times; (b) grouping in-time drift cell hits identified as being associated with a track of a particular charged particle passing through the detector; (c) initially estimating time zero for the particular charged particle; (d) determining drift radii based on estimates of time zero, drift time conversion data and the time of the hit; (e) fitting linear tracks to drift radii corresponding to a particular time-zero; and (f) searching and selecting a time-zero value associated with the best of the track fits performed for particular charged particle and computing error in time-zero and tracking parameters.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION

Figure 1:
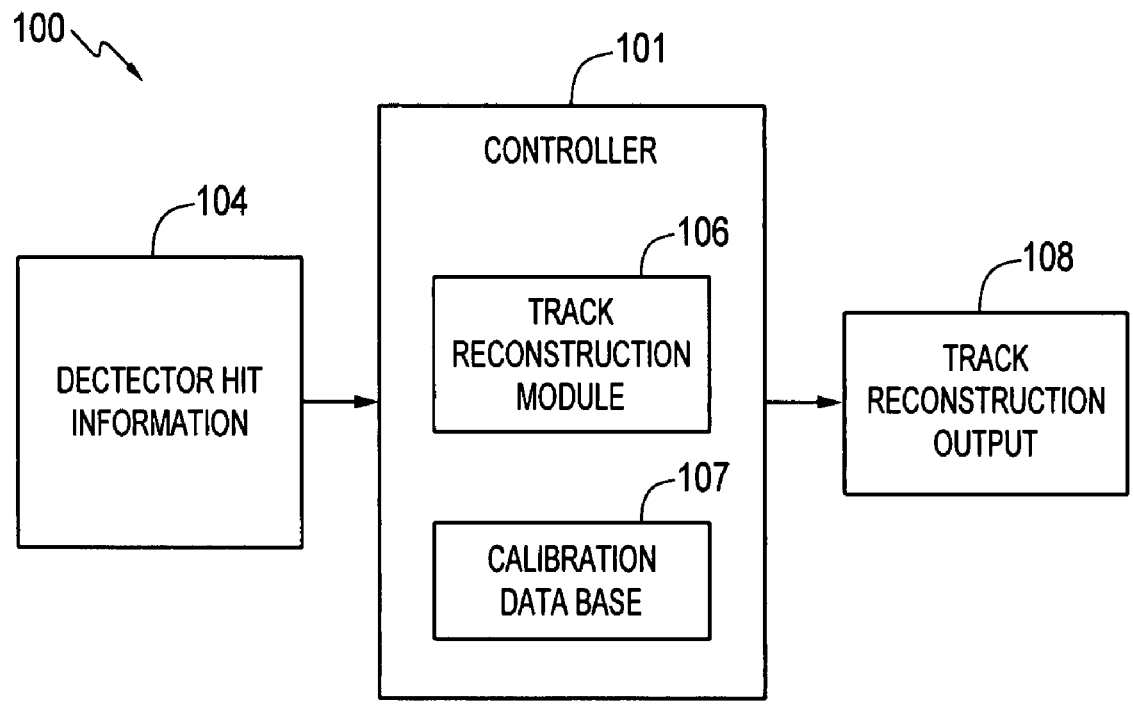
FIG. 1 illustrates a block diagram of a system for reconstructing a trajectory of a charged particle passing through a charged particle detector, according to one embodiment.

The particular values and configurations discussed in these non-limiting examples can be varied and are cited merely to illustrate at least one embodiment of the present invention and are not intended to limit the scope of the invention.

Technical features described in this application can be used to construct various particle detection systems. For example, a particle detection system for detecting muons as the charged particles can include an object holding area for placing an object to be inspected, a first set of position sensitive muon detectors located on a first side of the object holding area to measure positions and angles of incident muons towards the object holding area, a second set of position sensitive muon detectors located on a second side of the object holding area opposite to the first side to measure positions and angles of outgoing muons exiting the object holding area, and a signal processing unit, which may include, e.g., a microprocessor, to receive data of measured signals of the incoming muons from the first set of position sensitive muon detectors and measured signals of the outgoing muons from the second set of position sensitive muon detectors. As an example, each of the first and second sets of particle detectors can be implemented to include drift tubes arranged to allow at least three charged particle positional measurements in a first direction and at least three charged particle positional measurements in a second direction different from the first direction. The signal processing unit is configured to analyze scattering behaviors of the muons caused by scattering of the muons in the materials within the object holding area based on the measured incoming and outgoing positions and angles of muons to obtain a tomographic profile or the spatial distribution of scattering centers within the object holding area. The obtained tomographic profile or the spatial distribution of scattering centers can be used to reveal the presence or absence of one or more objects in the object holding area such as materials with high atomic numbers including nuclear materials or devices. Each position sensitive muon detector can be implemented in various configurations, including drift cells such as drift tubes filled with a gas which can be ionized by muons. Such a system can be used to utilize natural cosmic ray muons as the source of muons for detecting one or more objects in the object holding area.

The processing of measurements for cosmic ray-produced muons in a volume under inspection (e.g., a package, a container or a vehicle) by the processing unit can include reconstructing the trajectory of a muon through the volume, measuring the momentum of an incoming muon based on signals from the detectors on each side of the volume, and determining the spatial distribution of the scattering density of the volume. These and other processing results can be used to construct the tomographic profile and measure various properties of the volume such as detecting a target object.

For example, the reconstruction of the trajectory of a charged particle passing through a detector having a set of drift cells can include (a) receiving hit signals representing identifiers of drift cells hit by charged particles and corresponding hit times; (b) grouping in-time drift cell hits identified as being associated with a track of a particular charged particle passing through the detector; (c) initially estimating time zero for the particular charged particle; (d) determining drift radii based on estimates of time zero, drift time conversion data and the time of the hit; (e) fitting linear tracks to drift radii corresponding to a particular time-zero; and (f) searching and selecting a time-zero value associated with the best of the track fits performed for particular charged particle and computing error in time-zero and tracking parameters. Such reconstruction of the track based on the time zero fit provides a reconstructed linear trajectory of the charged particle passing through the charged particle detector without having to use fast detectors (such as photomultiplier tubes with scintillator paddles) or some other fast detector which detects the passage of the muon through the apparatus to the nearest few nanoseconds to provide the time-zero.

Also for example, the processing for measuring the momentum of an incoming or outgoing muon based on signals from the detectors can include, for example, (a) configuring a plurality of position sensitive detectors to scatter a charged particle passing therethrough; (b) measuring the scattering of a charged particle in the position sensitive detectors, wherein measuring the scattering comprises obtaining at least three positional measurements of the scattering charged particle; (c) determining at least one trajectory of the charged particle from the positional measurements; and (d) determining at least one momentum measurement of the charged particle from the at least one trajectory. This technique can be used to determine the momentum of the charged particle based on the trajectory of the charged particle which is determined from the scattering of the charged particle in the position sensitive detectors themselves without the use of additional metal plates in the detector.

Also for example, the spatial distribution of the scattering density of the volume can be determined from charged particle tomographic data by: (a) obtaining predetermined charged particle tomography data corresponding to scattering angles and estimated momentum of charged particles passing through object volume; (b) providing the probability distribution of charged particle scattering for use in an expectation maximization (ML/EM) algorithm, the probability distribution being based on a statistical multiple scattering model; (c) determining substantially maximum likelihood estimate of object volume density using the expectation maximization (ML/EM) algorithm; and (d) outputting reconstructed object volume scattering density. The reconstructed object volume scattering density can be used to identify the presence and/or type of object occupying the volume of interest from the reconstructed volume density profile. Various applications include cosmic ray-produced muon tomography for various homeland security inspection applications in which vehicles or cargo can be scanned by a muon tracker.

The methods and systems for reconstructing the trajectory of a charged particle through a charged particle detector according to the illustrative embodiments provides an approach in which the output from the charge particle detector is used to reconstruct the trajectory of the charged particles being detected without the need for fast detectors to determine the time of the charged particle encounter.

As will explained in more detail below, a detection system is described for reconstructing the trajectory of a charged particles passing through the object volume. This system includes a first set of position sensitive detectors located on a first side of an object volume to measure positions and angles of incident charged particles towards the object volume; a second set of position sensitive detectors located on a second side of the object volume opposite to the first side to measure positions and angles of outgoing charged particles exiting the object volume; and a signal processing unit to receive data of measured signals from the first set of position sensitive detectors and measured signals from the second set of position sensitive detectors. The signal processing unit processes the received data to construct the trajectory of a charged particle.

Figure 2:
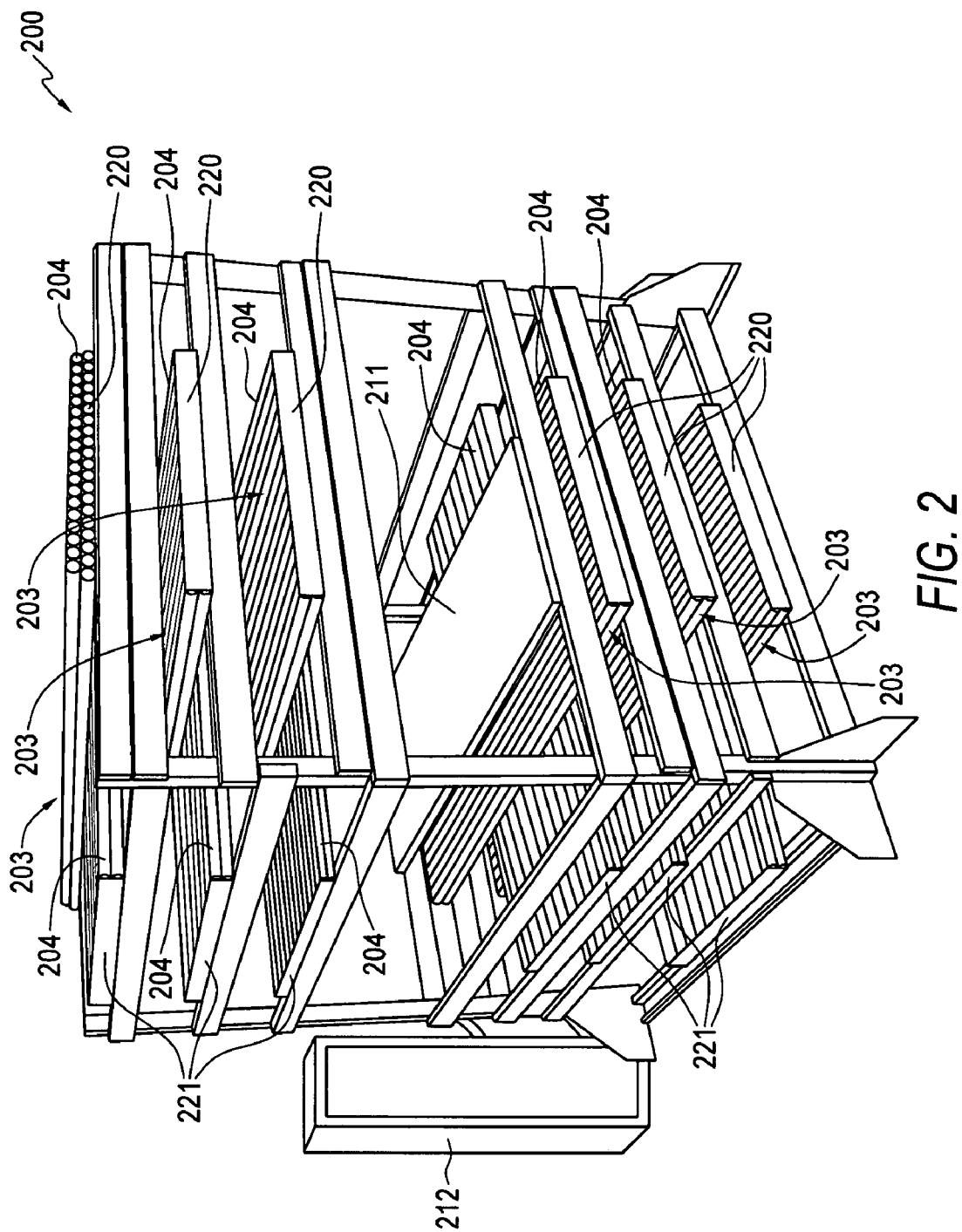
FIG. 2 illustrates a perspective view of an exemplary charged particle detector for providing charged particle information to the system of FIG. 1.

One example of charged particle detection system is a cosmic ray charged particle tracker which can be configured to track muons or other cosmic ray charged particles. One such muon detector is depicted in FIG. 2 which illustrates a detailed perspective view of a detector 200 which can be employed for cosmic ray-produced muon tomography of one or more packages, vehicles and cargo containers for various inspection and security monitoring applications including homeland security applications. These detectors must be large enough to fully encompass one or more packages, tractor-trailer trucks, vehicles of all sorts, and cargo containers.

A set of position sensitive detectors 203 are arranged above the sample holder plane 211 and another set position sensitive detectors 203 are arranged below the sample holder plane 211. Each set of position sensitive detectors comprises a double-layer 220 of drift tubes 204 arranged in the X direction and a double-layer 221 of drift tubes 204 arranged in the Y direction. In each of layers 220,221, the drift tubes 204 are arranged in two rows, offset by half a tube diameter from each other. Drift tube modules 204 are operable to detect cosmic ray muons and or other charged particles. In the system of FIG. 2, the drift tube modules are 12 foot long aluminum drift tubes which are configured to measure the position and angle of incoming and outgoing muon tracks in X and Y coordinate directions. Other position sensitive detector arrangements which provide a total of at least three individual positional measurements can be adopted instead of the arrangement of detectors of FIG. 2. At least 3 position measurements are required so as to enable a line fit.

Figure 6:
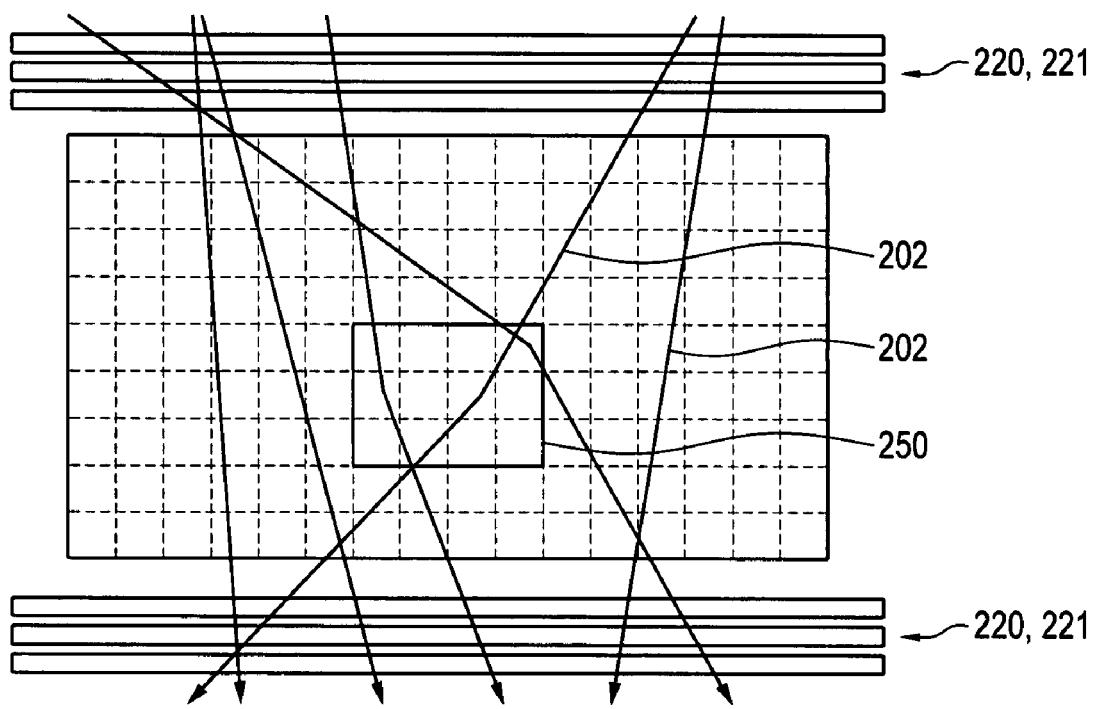
FIG. 6 illustrates a side view of the drift cells of the detector of FIG. 2 detecting muons passing through the detector.

Referring additionally to FIG. 6, which illustrates a side view of the position sensitive detectors of FIG. 2 arranged above and below an object 250 under interrogation, the position sensitive detectors 203 detect the incoming and outgoing muons which form tracks 202. On each side of the volume to be scanned, the drift tubes can be arranged to enable them to make at least three positional measurements in a first direction and in a second, different direction which may be orthogonal or non-orthogonal to the first direction. In some implementations, additional drift tube detectors can be implemented on sides of the volume to form a box or four sided structure into which a package, a vehicle or cargo container can enter for scanning by the system.

A signal processing unit, e.g., a computer, is provided in the system to receive data of measured signals of the incoming muons by the detectors above the object volume and outgoing muons by the detectors below the object volume. This signal processing unit is configured to analyze scattering behaviors of the muons caused by scattering in the volume based on the measured incoming and outgoing positions and angles of muons to obtain a tomographic profile or the spatial distribution of scattering centers within the volume. The obtained tomographic profile or the spatial distribution of scattering centers within the volume can reveal the presence or absence of the object in the volume. Thus, multiple scattering of cosmic ray muons can be used to selectively detect high z-material in a background of normal cargo. Advantageously, this technique is passive, does not deliver any radiation dose above background, and is selective to high-z dense materials. The tomographic processing part of the signal processing unit may be implemented in an on-premise computer that is at the same location with the detectors. Alternatively, the tomographic processing part of the signal processing unit may be implemented in a remote computer that is connected on a computer network such as a private network or a public network such as the Internet.

Data acquisition electronics 212 is configured to record the hit time and channel number of the drift tubes, where a "channel" corresponds to each drift tube in the system. The data acquisition electronics is configured to process the received data to construct the trajectory of a charged particle.

One example of the data acquisition electronics 212, operably coupled to the drift tubes, will now be described. Drift tubes of the detector system 200 of FIG. 2 are connected to respective electronic amplifiers (not shown) which increase the voltage of the deposited signal (associated with a cosmic ray-produced muon passing through a drift tube). For each drift channel, the amplified signal is turned into a digital signal with a piece of electronics called a discriminator (on if there is a hit, off if no hit), which preserves the precise time of the hit. This combination of amplifier and discriminator is the "front-end" electronics. The time and channel number that the digital signal is registered to the nearest nanosecond by the time-to-digital-converters (TDCs) mentioned above. Each drift tube has its own front-end electronics and TDC The front-end electronics is built using mostly hardware composed of off-the-shelf (OTS) parts. The TDC is OTS, and the units are built by Caen corporation in Italy. Each TDC unit (CAEN 767B) has the capability of 128 input channels (drift tubes in our case), and will store the time of the hit digitally. These units have a buffer which can hold about 32,000 hits. The TDCs are read-out about 5 times per second with a custom data-acquisition system (DAQ). The TDCs sit in a Versa Module Eurocard (VME) crate with a SIS 1100 controller, made by Struck Innovative Systeme GmbH (SIS), which provides the computer interface. The DAQ runs on a personal computer, with an optical cable to interface with the SIS 1100 to command the TDCs for the data transfer. Once the hit times and channel numbers are read out into the memory of the PC, the raw data is stored on hard drive, but the data is also processed to identify the cosmic ray events, and ultimately the time-zero-fitted tracks as explained below. The track data, and pertinent diagnostic data are also stored on the hard drive. All of this processing and track fitting is done real time, and is able to keep up with the approximately 200 Hz event rate.

Figure 4:
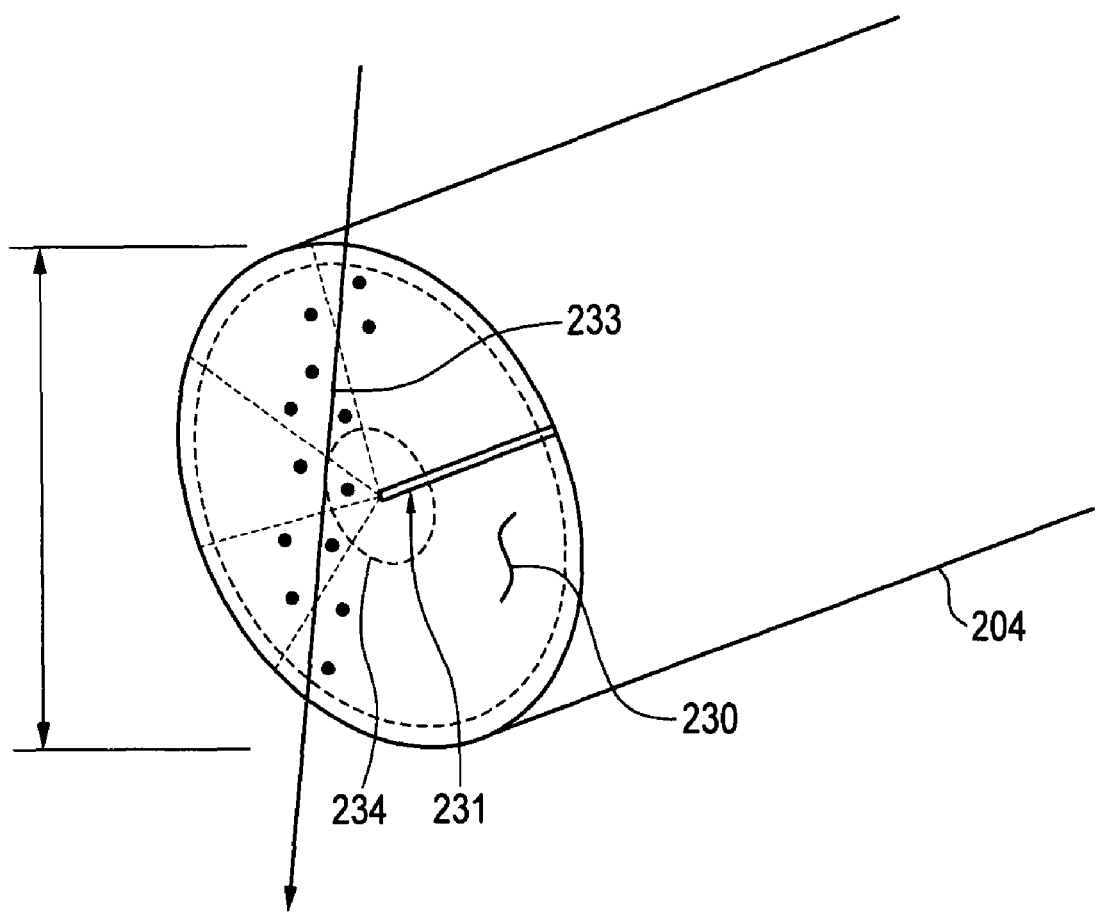
FIG. 4 is a cross-sectional view of part of typical drift tube of the charged particle detector of FIG. 1 indicating the distance of closest approach.

A cross-sectional view of part of a typical drift tube 204 detecting a muon or other charged particle passing through the tube is illustrated in FIG. 4. The drift tube module is typically cylindrical and filled with a detector gas such as Argon-Isobutane 230 to enable detection of the cosmic ray charged particles, such as muons. The system is configured to apply a positive HV of about +2-3 kV to a central anode wire 231 extending along the length of the cylindrical tube with the tube at ground so that a high-voltage static field is present. When the charged particle interacts with gas atoms, many electrons 233 are liberated from those drift-gas atoms in a straight line through a chord of the tube. The static field causes the "string" of electrons to drift toward the positively charged anode wire. The anode wire is typically very thin, 0.001" in diameter, creating a very high field near the wire to produce an electron avalanche when the first electron arrives. The avalanche of charge is about $10^5$ electrons per incoming electron that are easily detected with sensitive electronics. The anode wire is read-out electronically with the TDCS (time-to-digital converters) of the data acquisition electronics 212. This is how a hit signal is produced when a charged particle moves through the detector drift tube.

Whilst the drift tube of FIG. 4 is manufactured from aluminum, other materials such as carbon composite with internal conductive coatings can be adopted instead of aluminum. The drift tubes need not have circular cross-sections. For example, the drift tubes may be constructed from aluminum extrusions with multiple, non-circular cross-sections. Alternatively, drift cells other than drift tubes can be adopted such as for example triangular shaped drift cells. Drift cells having many anode wires, such as small gas drift chambers (GDC), can be used instead of using drift cells having a single anode wire. Furthermore, a drift cell may be another type of drift detector which employs the principle of electron or other particle drift for detection of charged particles hitting the detectors.

A typical operating set up of the detector 200 is as follows: 896 drift tube channels, 2300 volt operating voltage, drift gas 60% Ar/40% Isobutane, ~200 Hz trigger rate, 1.5 m tall sample area. Typical drift time of 1600 nanoseconds.

An example of an automated system for reconstructing the trajectory of a charged particle according to one embodiment is illustrated in block diagram in FIG. 1. Automated system 100 has a controller 101 adapted and arranged to receive detector hit information 104 and to provide track reconstruction output 108. The controller can be a signal processing unit which can be integrated in the data acquisition unit of the detector or can be remote from the detector. The information 104 can be hit signals from the cosmic ray muon detector of FIG. 2, or alternatively, can be from any other charged particle detector having drift cells enabling tracking of a charged particle interacting with the drift cells. In any case, the hit signals are data collected from each drift cell and represent: 1) time that the hit is collected by the electronics relative to a consistent but arbitrary origin, and 2) drift cell channel number (or other identifier) of hit.

Automated system 100 includes a track reconstructor module 106 and calibration data base 107 stored on the controller. Predetermined drift cell positional information is stored in the calibration data base. Track Reconstructor module 106 is responsible for reconstructing the trajectory of the charged particle passing through the detector. The module may be software or hardware In the illustrative embodiment of the automated system 100 of FIG. 1, the controller 101 is any kind of computer processor unit (CPU) based system such as a personal computer (PC), or other microprocessor based system such as a digital signal processor based system. An operating system runs on the controller 101 and may be a commercially available or open-source operating system. Instructions for the operating system and applications or programs are stored in storage devices, such as a hard drive. A user interface (not shown) can be operably connected to the processing system to allow a human operator to manipulate the processing system, as required. Also, in the automated system 100, the track reconstructor module 106 is software in the form of a computer-usable data carrier storing instructions that, when executed by the controller, cause the controller to perform a method of reconstructing the trajectory of a charged particle passing through a detector having a plurality of drift cells. The module can be installed locally on the controller, as indicated in FIG. 1, or run from a remote location via a network coupled to the controller. Those skilled in the art would understand there are multiple modes of implementing such a module.

Those skilled in the art would understand that the illustration of FIG. 1 is merely depicting one example of the embodiments and that the embodiments are not limited thereto. For example, some or all of the track reconstructor module functionality can be implemented as hardware such as analogue or digital circuitry without the use of microprocessor.

In order to track a cosmic ray-produced muon or other charged particle traveling through a given drift tube detector, the closest approach, otherwise known as the "drift radius", between the muon and the detector anode wire running down the axis of the tube (see for example dotted inner circle 234 of FIG. 4 which corresponds to the radius of closest approach) must be determined. The distance of closest approach and the position of the tube along with the other tubes that have been hit by the charged particle are required to reconstruct, by computation, a 3D linear track of the charged particle passing through the system of detectors. The closet approach is found by converting the drift time of the electron drift to the anode wire to a distance. The drift distance is needed to fit the linear tracks through the system when a muon passes through. The drift distance is a function, $R=R(Ti-T0)$, where Ti is the time that the drift electron arrived at the wire of a particular hit, and T0 is the time-zero (when the "stopwatch" begins). T0 is common to all of the hits in a given muon track event, and must be measured or found for each muon track event. One cannot know this drift distance unless the travel time of the free electrons to the anode is known. For example, a cylindrical gas-filled drift tube such as that of FIG. 4 has a total drift time of 1-2 microseconds, depending on detector shape, size, drift gas, and anode voltage. In order to determine the electron travel time, the time at which the charge particle actually went through the detector, referred to herein as time-zero, is required.

Figure 3:
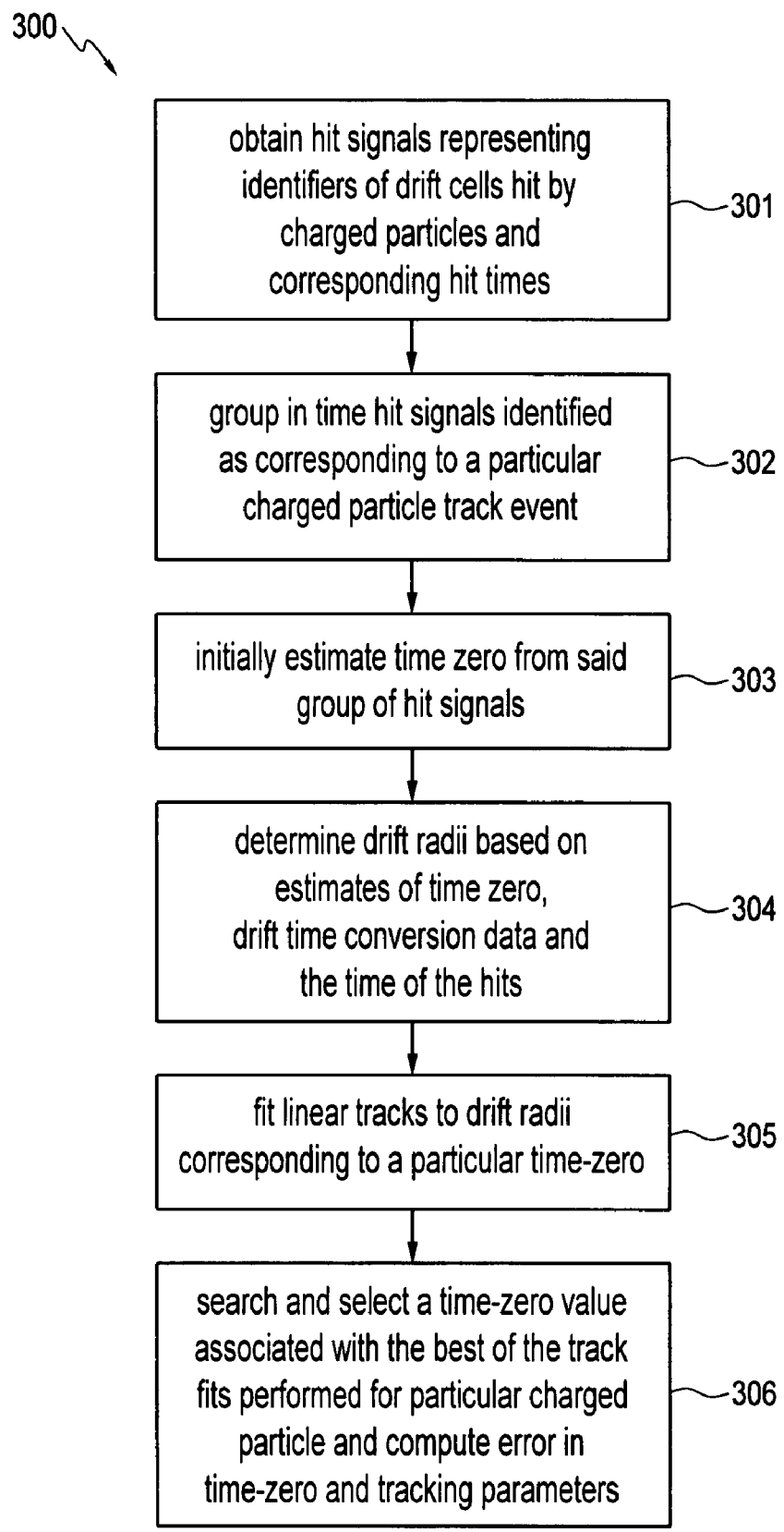
FIG. 3 illustrates a flow chart generally outlining a method of reconstructing a trajectory of a charged particle passing through a charged particle detector according to an embodiment.

A method for reconstructing the trajectory of a charged particle passing through a charged particle detector according to one embodiment will now be described. FIG. 3 illustrates a flow chart generally outlining the method for reconstructing the trajectory of a charged particle passing through a charged particle detector.

Method 300 initiates and the hit signals representing identifiers of drift cells hit by charged particles and corresponding hit times are received, as indicated in process step 301. The hit signals are grouped in time to make a track event through the detector. The hits in an event will have a variation over the maximum drift time, since some hits will be close to an anode wire and some will be near the outer edge of the drift cell. To this end, hit signals identified as corresponding to a particular charged particle event are grouped in time, typically within a 2 microsecond window, as indicated in process step 302, where 2 microseconds is the approximate maximum drift time of an electron very near the tube wall.

The fitting of time-zero is intimately tied to the fitting of a track to match the most likely path of the charged particle through the detector. An initial guess or estimation of the time zero for the particular charged particle is made from the grouped hit signals, as indicated in process step 303. As indicated in process step 304, drift radii are determined based on estimates of time zero, drift time conversion data and the time of the hit. Linear tracks are fit to drift radii corresponding to a particular time-zero, as indicated in process step 305. The path of the muon is assumed to be linear through the top and bottom regions separately even if the path of the muon may be diverted by high-density material in the scanning region. Therefore, the fits of the muon path are to the direction cosines of a line in space. A time-zero associated with the best of the track fits performed for particular charged particle are searched and selected and the error in time-zero and tracking parameters computed, as indicated in process step 306.

Fitting time zero uses a set of hits identified as corresponding to an event window such as for example a 2 microsecond event window. Reconstructing the track based on the time zero fit provides a reconstructed 3-D linear trajectory of the charged particle passing through the charged particle detector without having to use fast detectors (such as photomultiplier tubes with scintillator paddles) or some other fast detector (which actually detects the passage of the muon through the apparatus to the nearest few nanoseconds) to provide time-zero. As the method for reconstructing the trajectory of the charged particle according to the illustrative embodiments utilize as much information as possible from the aggregate drift tube data for a given track, the method avoids having to obtain measurements from fast detectors, particularly, photomultiplier tube and scintillator paddles arrangements.

The large size and number of drift tubes in applications for scanning large objects such, as vehicles or cargo containers, requires many square meters of fast detectors to determine time-zero and, in turn, the trajectories of charged particles. Generally, fast detectors do not have much in the way of spatial resolution and are not as efficient as well-behaved position sensitive detectors. The fast detectors also tend to be lower in efficiency (only detect 80% or so of charged particles), so that higher exposure time for a container or truck scan is required. Fast detectors are therefore not as good at time-zero fitting as the method and system of the illustrative embodiments and are more expensive.

Figure 3A:
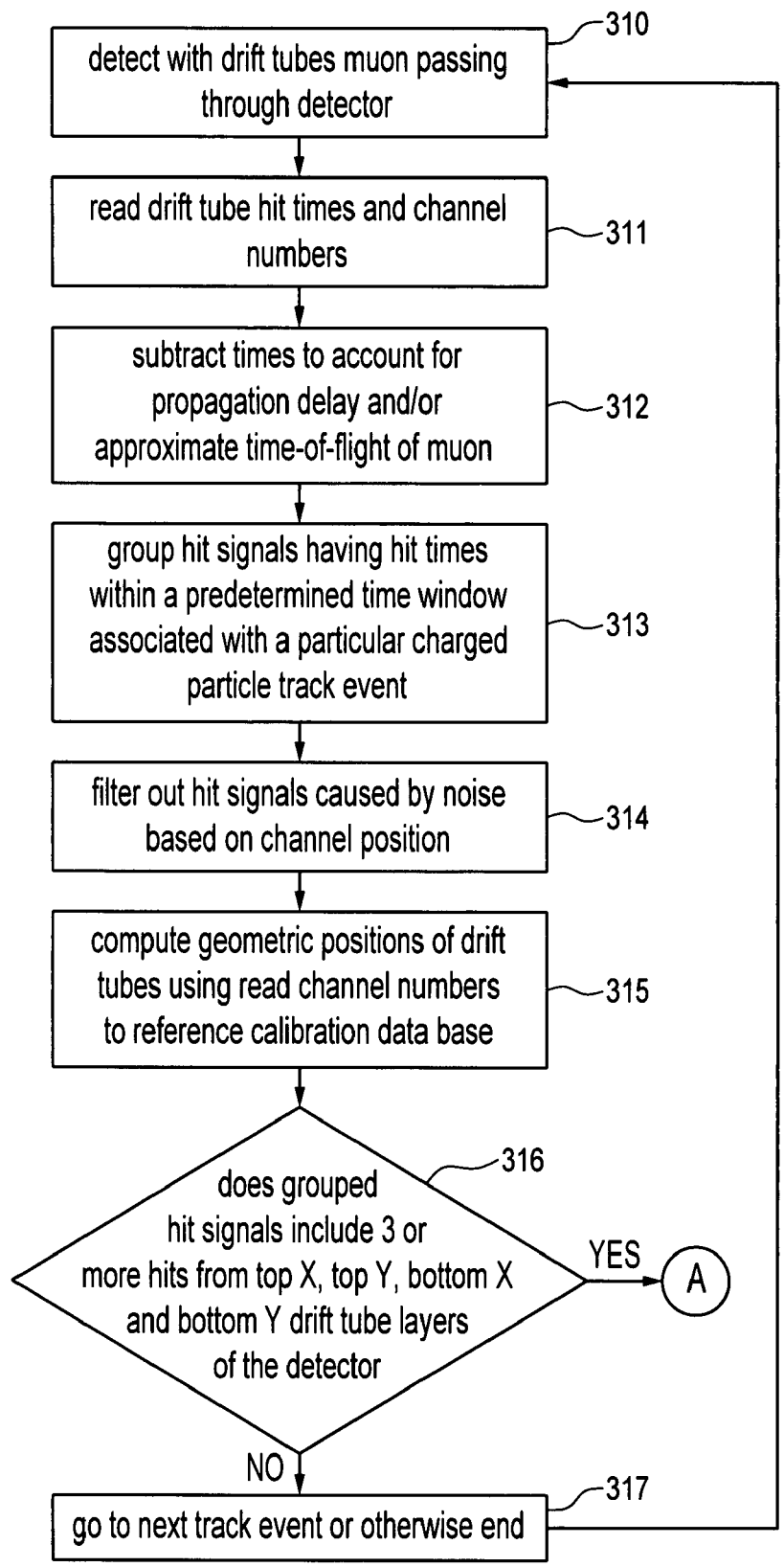
FIGS. 3A-3C illustrate a flow chart showing in detail the method of FIG. 3 according to one embodiment.
Figure 3B:
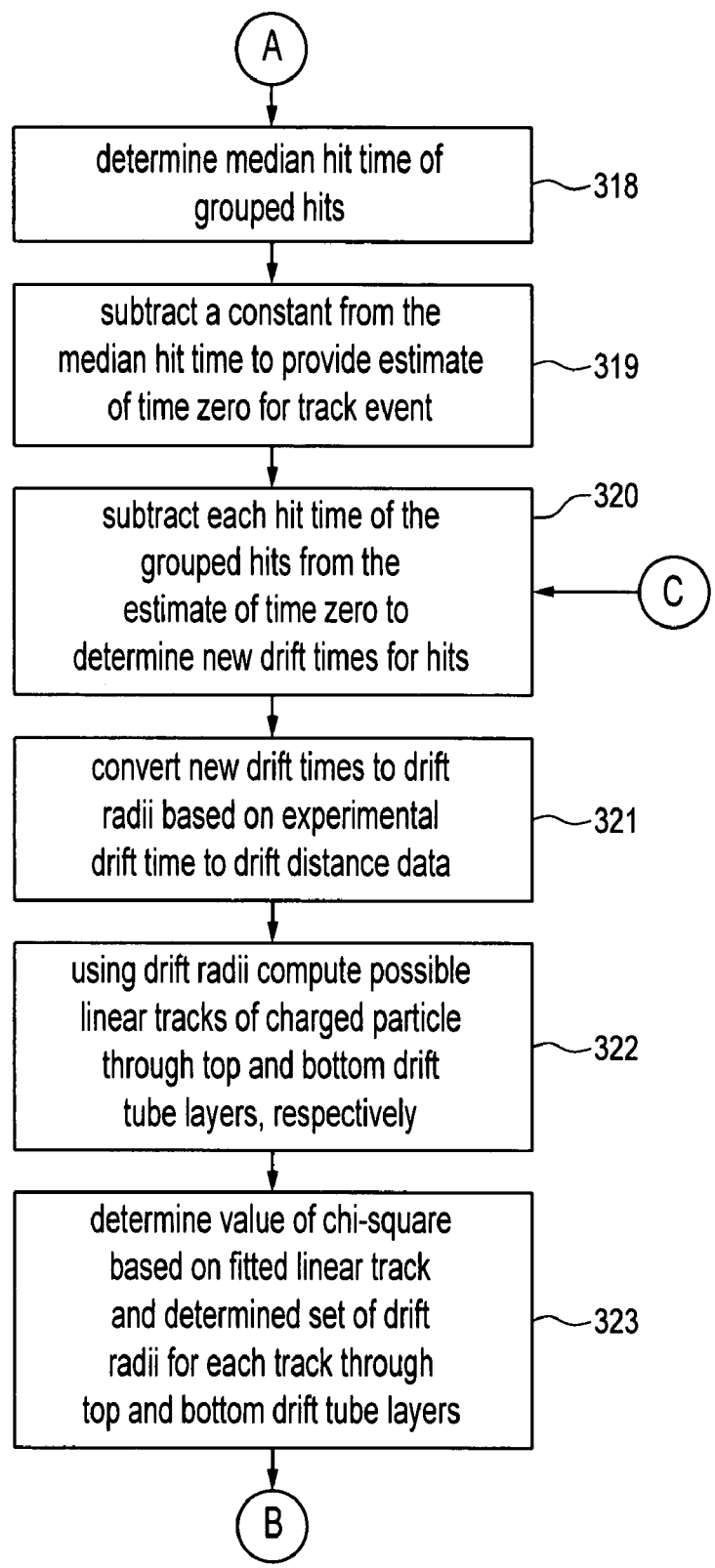
Figure 3C:
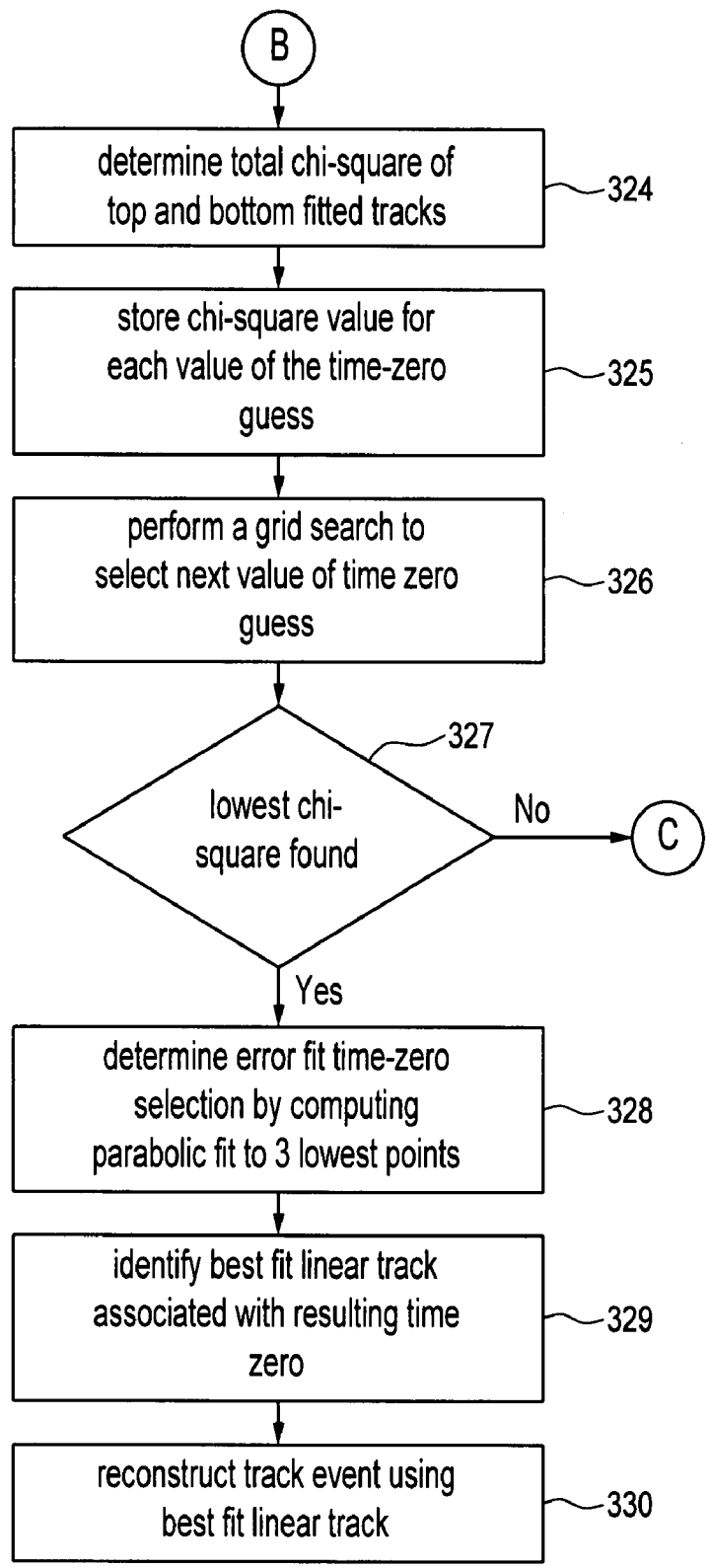
Figure 7:
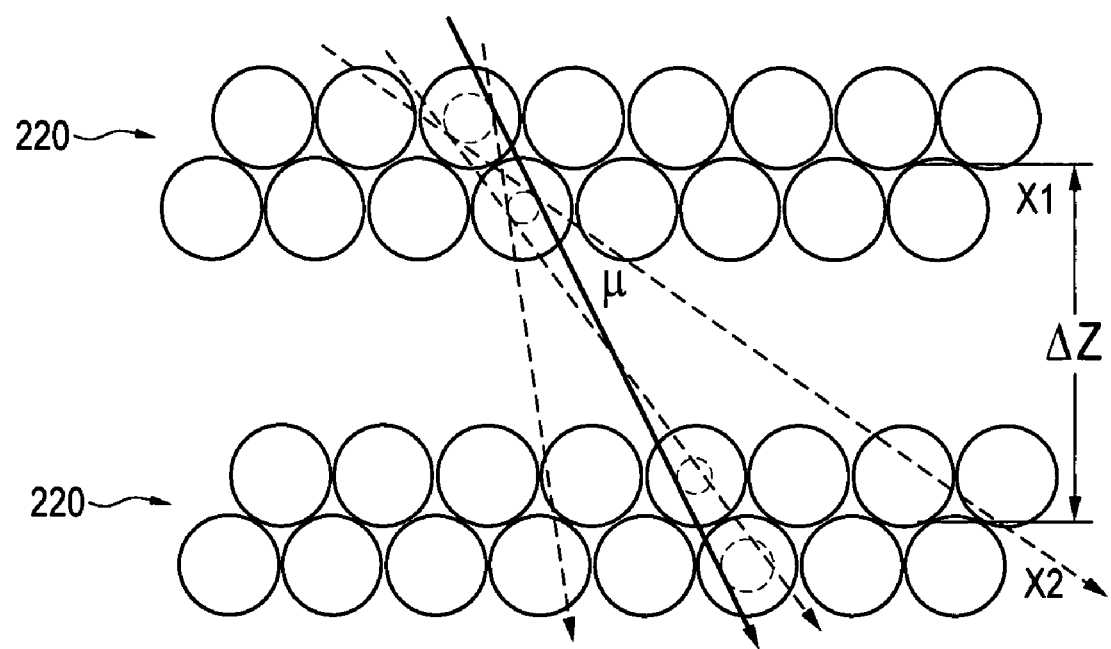
FIG. 7 illustrates an exemplary muon trajectory to be reconstructed together with theoretical linear tracks fitted using the method of FIG. 3.

Referring now to FIGS. 3A-3C which illustrate flow charts showing in more detail, the method 300 will now be described. The method 300 can be implemented in the automated system 100 of FIG. 1 using hit signals 104 from the detector 200 of FIG. 2 to reconstruct the trajectory a cosmic ray muon passing through the detector 200. By way of example, let us assume the muon trajectory to be reconstructed is the muon track 202 shown in FIG. 7 passing through the drift tube layers 220.

The hit signals 104 represent a cosmic ray (CR) muon which has reached the detector and has passed through several of the small gas drift chambers (GDC). Generally speaking, in order to have enough information for a track to be reconstructed the detector output data should include hit signals representing the muon passing through 6 or more drift tubes (3 or more for each tube direction). It is also assumed that the mean cosmic ray-produced muon energy is 3 GeV; hence it will travel in an approximately straight line through the drift cells because the associated material is relatively transparent to the CR muon over a wide range of energies. The muon at this energy will travel through an areal density of 1500 g/cm$^2$ (about 1.3 meters of lead, or 5.5 meters of aluminum). Furthermore, it is assumed that the muon is traveling near the speed of light (0.9994c or about 1 foot/nanosecond), so for the sake of simplicity we can ignore the time-of-flight (TOF) for muons within the drift tube. It is also further assumed that the accurate positions and orientations of the drift cells in the system are already known and stored in the calibration data base.

Referring now to FIG. 3A, process steps 310-312 describe in detail the step of obtaining hit signals (process step 301 of method 300) according to one embodiment. The cosmic ray-produced muon passing through the detector 200 is detected by the drift cells of the detector 200, as indicated in process step 310. The controller 101 reads the resulting hit signals 104, which represent drift cell channel numbers of the hits and corresponding hit times, from the data acquisition (DAQ) hardware 212 (see FIG. 2) of detection system 200 (process step 311). If required, the controller then subtracts times to account for propagation delay and/or approximate time-of-flight of muon, as indicated in process step 312.

Process steps 313 to 317 of FIG. 3A describe in detail the process of grouping in time hit signals identified as corresponding to a particular charged particle track event (process step 302 of FIG. 3) according to one embodiment. As indicated in process step 313, hit signals having hit times within a predetermined time window associated with the track event are grouped together. The time window is predetermined so as to select hit times of hits from a given event which range in position from close to the anode to near the outer edge of the drift cell caused by the particular charged particle track event. For example, for a typical small gas drift chamber of the detector of FIG. 2, the time window is about 2 microseconds. This time window is determined experimentally, and depends on the physical details of the drift chamber design, drift gas used and applied high voltage.

As indicated in process step 314, noise hit signals are filtered out based on channel position information. To this end, ignoring the drift radius and considering channel position only, the reconstructor module filters out hits which cannot possibly lie on a line with the predominant group of hits. These are considered to be "noise" hits, and filtering them out helps the fitter converge to a solution and to ignore spurious hits.

In process step 315, geometric positions of each channel are computed by the controller using the channel number to reference predetermined information held in the calibration database 107. The positional calibration maps the hit channel number to predetermined geometric positional data held in the calibration data base.

As indicated in process step 316, a determination is made as to whether the grouped hit signals include 3 or more hit signals for top X, top Y, bottom X, bottom Y drift tube layers of the detection system 200, as is required for the purpose of reconstructing a track event. These 3 or more hit signals belong to "fitgroups" of the muon tracker detector system 200 and detector systems that have distinct orthogonal or component directions. If the group of hit signals representing the track event does not include enough hit signals, that is, does not include 3 or more hit signals generated by top X, top Y, bottom X, bottom Y layers of the system, the process skips the remaining process steps 303-306 and goes to the next track event, as indicated in process step 317. Process step 313 then recommences using hit signals for the next event. If however, the grouped hit signals do include enough hit signals, the group of hit signals is passed on and the process continues to process step 303 of method 300 (see FIG. 3B) for the purpose of initially guessing time zero.

Referring now to FIG. 3B, process steps 318 and 319 describe in detail the process step of initially guessing time zero (process step 303 of method 300) according to one embodiment. In order to produce an initial guess of time-zero the median time of the grouped, noise-filtered hit signals is first determined, as indicated in process step 318. The reason for this initial guess is to get to a starting value of time-zero which isn't too far numerically from the expected solution. This also helps the fitter to converge more quickly.

Thereafter, a constant is subtracted from the median hit time to provide the first initial guess of time zero for the track, as indicated in process step 319. The closer the initial guess, the more likely and more rapidly the $T_0$ search will converge. The median is a more stable statistic than is the mean, since it is not greatly affected by large excursions from the main population of hits. This constant is determined empirically during the calibration process by plotting the difference between the median time and the fitted time zero ($T_0$) for a large population of track fits. This $T_{median}$-$T_0$ constant will vary depending on the detector size, shape, gas, and anode voltage, and is best measured in the initial calibration. For example, for the case of the detector tubes of the detector of FIG. 2, the constant is about 504 ns. This number represents the most likely difference between the median of the selected population of drift tube hits and the fitted $T_0$ which will occur for the current track. For example, a given group of hits will have a median, $T_{median}$. The first guess of $T_0$ will be found by the expression: $T_{median}$-504 ns.

In process steps 318 & 319 of the illustrative embodiment, the median hit time is determined and used because the median is a much more robust estimator than the mean, since it is far less affected by large outliers. However, in alternative embodiments, process steps 318 & 319 can instead determine and use the mean or other metric of the grouped hit times. Furthermore, other methods can be used to obtain the first guess of time zero. For example, the time of the first hit can be used to guess time zero. The problem with the latter technique is that uncorrelated noise hits bias that first hit time to be potentially earlier than it should for the group hits, hence the superiority of the median technique.

Process steps 320 to 322 of FIG. 3B illustrate in more detail process steps of 304 and 305 of method 300 according to one embodiment.

As will be explained in more detail below, fitting linear tracks to drift radii may be based on linear regression formulas or an iterative fit which minimizes the aggregate distance from track to anode wire. In the illustrative embodiment, the fitting process uses a chi-square test for goodness of fit of the computed distribution of tracks to a theoretical chi-square of one per degree of freedom, where degrees of freedom is the total number of hits minus number of fit parameters, 8: 4 parameters for each of the top and bottom tracks.

The reconstructor module fits the linear tracks to a 3-dimensional line through the top and bottom sections of the detector separately based on the list drift radii just computed. Recall that we are interested in the bend angle of the muon, and that bend angle is a comparison of the top-fitted linear track and the bottom-fitted linear track. The bend angle will later be used for density reconstruction of the object(s) in the scanning region of the detector.

The overall track fit will yield the minimum value of the sum of the squares of the weighted difference between the fitted track and the measured set of drift radii. This quantity is called the chi-square ($\chi^2$), and the fitter must minimize its value.

$$\chi^2 = \sum_{i=1}^{N}\left(\frac{x_i - f(\vec{a}, z_i)}{\sigma_i}\right)^2,$$

where i is the hit index, N is the number of hits in the event, $x_i$ is the projection of the drift radius to the anode wire position, $z_i$ is the dependent variable (in this embodiment the vertical position of the $i^{th}$ anode wire) of the linear equation for the line, $f(\vec{a}, z_i)$, the vector, $\vec{a}$, is the set of eight (8) slope and intercept parameters of the fitted tracks through the top and bottom sections of the detector system, $\sigma_i$ is the resolution (measured during the calibration process) of the individual drift wire. Examples of track fitting are disclosed in a publication entitled "Data Reduction and Error Analysis for the Physical Sciences", issued as $3^{rd}$ edition, 2002 of Bevington and the contents of which are incorporated herein by reference.

Turning then to process step 320 of FIG. 3B, the current value of the time zero guess is subtracted from every hit time in the grouped hit list in order to determine the drift time of each hit. It is assumed that the top and bottom tracks, that is, the tracks resulting from the muon passing through the top and bottom drift tubes, respectively, correspond to the same time zero.

Figure 5:
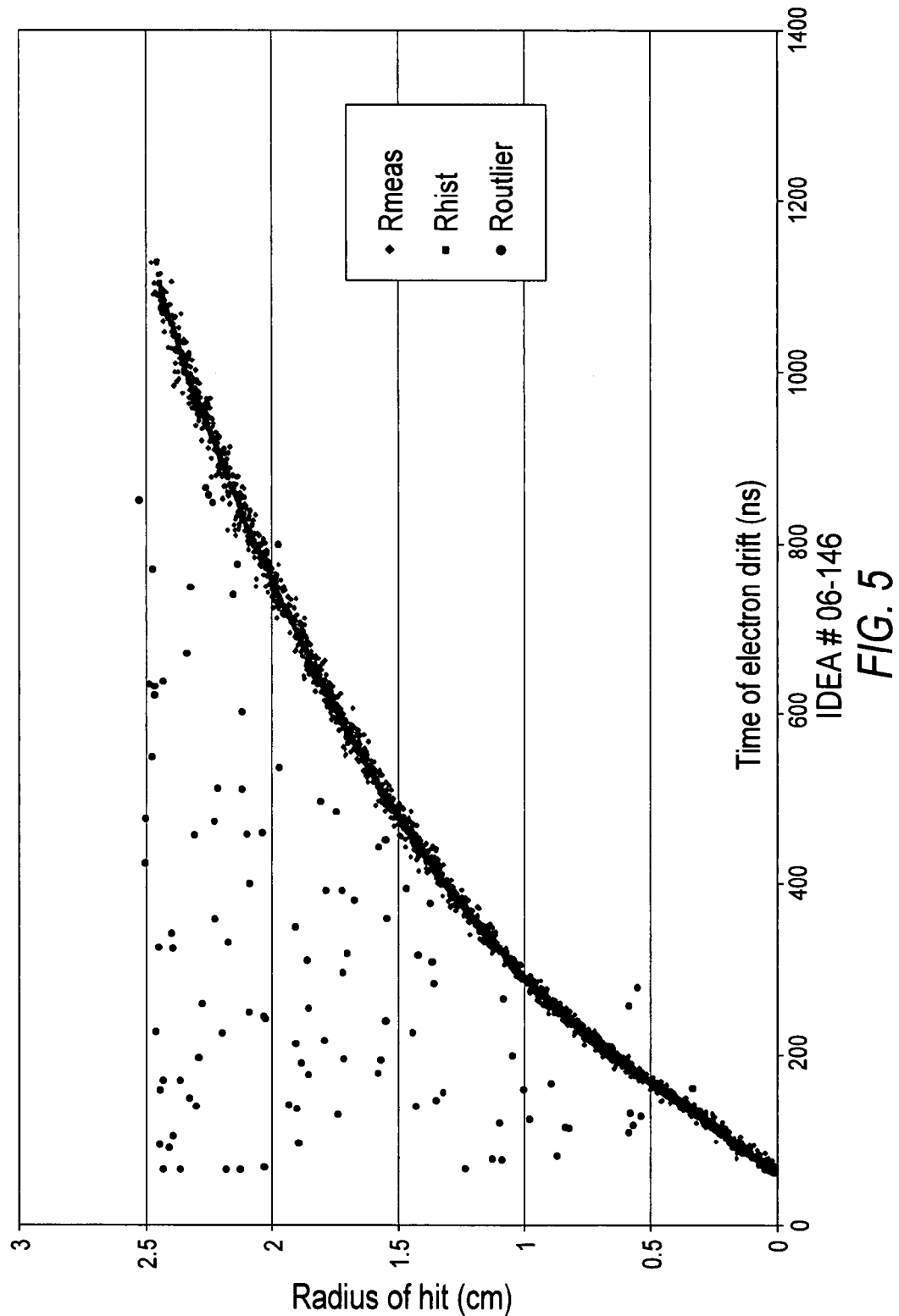
FIG. 5 is a typical example of experimentally predetermined drift time to drift distance curve for use in the method illustrated in FIG. 3.

Thereafter, the list of subtracted times, that is, the drift times determined in previous step 320, are converted to drift radii based on experimental drift time to drift distance data, as indicated in process step 321 FIG. 5 shows an example graph of drift time to drift distance data that is used to convert drift time to radius (the main fitted line). This curve is predetermined experimentally, and contained in the calibration database. Given the time-to-distance curve (the predominant curve in FIG. 5), the drift time of the first electron to the anode wire is required to perform the conversion, which requires the time that the charged particle actually went through the detector, that is, time zero. Muon travel time is neglected since the drift velocity of the ionized electrons is <0.01% of the muon speed. The computation of drift radius is why the time zero of the event is so vital. The drift radii of the event are what ultimately turn into the estimated linear path of the muon through the set of drift tubes.

Thus, as indicated in process step 322, theoretical linear tracks of charged particle through top and bottom drift tube layers, respectively, are computed by the reconstructor module using the drift radii calculated in process step 321 and geometric positions of the drift cells computed in process step 315.

Process steps 323 to 330 of FIGS. 3B & 3C illustrate in more detail process step 306 of method 300 according to one embodiment. As indicated in process step 323, the process continues by determining the value of chi-square of the fitted track relative to the measured set of drift radii. Thereafter, the total chi-square of the top and bottom fitted tracks is computed, as indicated in process step 324. We record one-to-one the value of chi-square for each value of the time-zero guess, as indicated in process step 325. Thereafter, a grid search is performed to find the value of time-zero which corresponds to the lowest possible value of chi-square (process step 326).

The chi-square values can be stored in formats other than tables and searched by methods other than grid searching.

If the lowest chi-square is not found, then, as indicated in process step 327, the process returns to process step 320 of FIG. 3B and for each value of the time-zero guess, the drift time for each hit is recomputed by repeating process steps 320 through 326 using the value of time-zero guess. It is assumed that each time-zero guess is the time-zero common to all selected hits. Each time-zero guess will have an associated track chi-square. The best guess will be associated with the lowest track chi-square. A typical fit will result in 20 or so time-zero guesses (and associated chi-square) before a final decision is made. Once the lowest chi-square is found (see also process step 327), the process continues to the next process step 328 in which the error of the time-zero selection is determined by computing a parabolic fit to the lowest 3 points. The error value corresponds to the change in time-zero that results in an increase in chi-square of 1.0. This is standard statistical procedure. The typical error value is on the order of 10 nanoseconds or less. Thereafter, the good linear fit for resulting time-zero is selected (process step 329) and the path of the muon is reconstructed using the good fit linear track (process step 330).

As already indicated, method 300 enables reconstruction of a track without having to fully instrument the drift tube detector with fast scintillator which is quite expensive. In addition, this PMT/scintillator arrangement can be a temporary part of the detector, to be removed following initial calibration. The lack of a major amount of scintillator paddles and associated PMTs makes engineering of the detector cheaper. Fewer electronics channels will also result (also making the detector cheaper and easier to read out and understand). The PMTs and associated electronics may add a significant amount of electronic noise further complicating the readout of the drift tube detectors. The scintillator/PMT combination conventionally required is significantly less efficient (ranging from 50-70%) than drift tubes (>99% within the gas volume). Thus if scintallators were required for tracking, then this would pull down the overall efficiency of the detector.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only.

Other variations and modifications of the present invention will be apparent to those of skill in the art, and it is the intent of the appended claims that such variations and modifications be covered.

The description as set forth is not intended to be exhaustive or to limit the scope of the invention. Many modifications and variations are possible in light of the above teaching without departing from the scope of the following claims. It is contemplated that the use of the present invention can involve components having different characteristics.

The invention claimed is:

1. A method for reconstructing the trajectory of a charged particle passing through a charged particle detector having a plurality of drift cells, said method comprising:
   (a) obtaining hit signals representing identifiers of drift cells hit by charged particles and corresponding hit times;
   (b) grouping in-time drift cell hits identified as being associated with a track of a particular charged particle passing through said detector;
   (c) initially estimating time zero for said particular charged particle;
   (d) determining drift radii based on estimates of time zero, drift time conversion data and the time of the hit;
   (e) fitting linear tracks to drift radii corresponding to a particular time-zero; and
   (f) searching and selecting a time-zero value associated with the best of the track fits performed for particular charged particle and computing error in time-zero and tracking parameters.

2. The method of claim 1, wherein said charged particle comprises a muon.

3. The method of claim 1, wherein initially estimating time zero for said particular charged particle comprises
   initially estimating time zero for said particular charged particle from said grouped hits.

4. The method of claim 1, wherein obtaining hit signals representing identifiers of drift cells hit by charged particles and corresponding hit times comprises
   reading times of said drift cell hits;
   reading corresponding drift cell channel numbers; and optionally
   subtracting times to account for propagation delay and/or approximate time of flight of particular charged particle.

5. The method of claim 4, wherein grouping in-time drift cell hits identified as being associated with a track of a particular charged particle passing through said detector comprises
   grouping hit times within a predetermined time window associated with said track; and
   including only those hits most likely to be part of the particular charged particle track.

6. The method of claim 1, wherein initially estimating time zero for said particular charged particle comprises
   determining the metric based upon hit times of said grouped hits; and
   subtracting a constant from the metric hit time.

7. The method of claim 6, wherein determining the metric hit time comprises
   determining the median hit time of said grouped hits.

8. The method of claim 1, wherein fitting linear tracks to drift radii corresponding to a particular time-zero includes fitting said tracks to drift radii using linear regression formulas or an iterative fit in order to minimizes the aggregate distance from a track to anode wire of the drift cell.

9. The method of claim 1, wherein determining drift radii based on estimates of time zero, drift time conversion data and the time of the hit comprises
   subtracting each hit time of the grouped hits from said initial estimate of time zero to determine each drift time of each hit; and
   converting said drift times to radii based on predetermined experimental/theoretical drift time to drift distance data stored in a database.

10. The method of claim 1, wherein obtaining hit signals representing identifiers of drift cells hit by charged particles and corresponding hit times comprises
   obtaining hit signals from a first set of drift cells positioned on a side of an object volume to measure the position of incoming charged particles entering the object volume; said first set of drift cells having drift cells configured in a first component direction and in a second component direction; and
   obtaining hit signals from a second set of drift cells positioned on a side of an object volume to measure the position of outgoing charged particles exiting the object volume; said second set of drift cells having drift cells configured in a first component direction and in a second component direction.

11. The method of claim 10, further comprising
determining if said grouped hits include at least three hit signals from said first set drift cells positioned in a first component direction and at least three hit signals from said first set drift cells positioned in a second component direction;
determining if said grouped hits include at least three hit signals from said second set drift cells positioned in a first component direction and at least three hit signals from said second set drift cells positioned in a second component direction; and
grouping in-time drift cell hits identified as being associated with a next track of a particular charged particle passing through said detector in response to determining said grouped hits do not include each of said at least three hit signals.

12. The method of claim 10, wherein fitting linear tracks to drift radii corresponding to a particular time-zero includes
fitting linear tracks of charged particles passing through said first set and said second set of drift cells, respectively, using obtained drift radii; and
wherein searching and selecting a time-zero value associated with the best of the track fits performed for particular charged particle and computing error in time-zero and tracking parameters comprises
estimating each next time zero from track fits for said first and second drift cell sets; and
for each next time zero, determining drift radii based on estimates of time zero, drift time conversion data and the time of the hit, and fitting linear tracks to drift radii corresponding to time-zero until a substantially linear track having a best fit to most likely or expected path of charged particle passing through detector is obtained.

13. The method of claim 10, wherein fitting linear tracks to drift radii corresponding to a particular time-zero includes
fitting linear tracks of charged particles passing through said first and second sets of drift cells, respectively, to obtained drift radii; and
wherein searching and selecting a time-zero value associated with the best of the track fits performed for particular charged particle and computing error in time-zero and tracking parameters comprises
determining a minimum value of chi-square based on track fits for said first set and second set of drift cells and said drift radii;
adding together chi-squares for fitted tracks to determine total chi-square;
storing chi-square value for each estimate of value of time-zero;
performing a search to determine time-zero corresponding to the lowest estimated value of chi-square; and
determining a parabolic fit to at least three lowest points to determine error of time-zero selection; and
determine linear track using correct time-zero selection.

14. A system for reconstructing the trajectory of at least one charged particle passing through a detector having a plurality of drift cells, said system comprising a controller adapted and arranged to:
(a) obtain hit signals representing identifiers of drift cells hit by charged particles and corresponding hit times;
(b) group in-time drift cell hits identified as being associated with a track of a particular charged particle passing through said detector;
(c) initially estimate time zero for said particular charged particle;
(d) determine drift radii based on estimates of time zero, drift time conversion data and time of the hit;
(e) fit linear tracks to drift radii corresponding to a particular time-zero; and
(f) search and select a time-zero value associated with the best of the track fits performed for particular charged particle and compute error in time-zero and tracking parameters.

15. The system of claim 14, wherein said charged particle comprises a cosmic ray charged particle.

16. The system of claim 14, further comprising a charged particle detector operably coupled to said controller, said charged particle detector having a first set of drift cells positioned on one side of an object receiving volume to measure positions of incoming charged particles entering the object volume, and having a second set of drift cells positioned on another side of the object volume to measure positions of outgoing charged particles exiting the object volume; and
wherein said controller is adapted and arranged to receive hit signals and corresponding hit times from said first set of drift cells and said second set of drift cells.

17. The system of claim 16, wherein said controller is adapted and arranged to:
fit linear tracks of charged particles passing through said first set and said second set of drift cells, respectively, to obtained drift radii;
determine a minimum value of chi-square based on track fits for said first and second sets of drift cells and said drift radii;
add together chi-squares for said fitted tracks to determine total chi-square;
store chi-square value for each estimate of value of time-zero;
perform a search to determine time-zero corresponding to the lowest estimated value of chi-square;
determine a parabolic fit to at least three lowest points to determine error of time-zero selection; and
determine linear track using correct time-zero selection.

18. The system of claim 14, wherein said controller is adapted and arranged to
group hit times within a predetermined time window associated with said track; and
include only those hits most likely to be part of the particular charged particle track.

19. The system of claim 18, wherein said controller is adapted and arranged to
determine the metric based upon hit times of said grouped hits; and subtract a constant from the metric hit time in order to provide an initially estimate time zero.

20. The system of claim 18, wherein said controller is adapted and arranged to
subtract each hit time of the grouped hits from said initial estimate of time zero to determine each drift time of each hit; and
convert said drift times to radii based on predetermined experimental/theoretical drift time to drift distance data stored in a database.

21. A computer program product comprising: a computer-usable data carrier storing instructions that, when executed by a computer, cause the computer to perform a method for reconstructing the trajectory of a charged particle passing through a detector having a plurality of drift cells, said method comprising:

(a) obtaining hit signals representing identifiers of drift cells hit by charged particles and corresponding hit times;
(b) grouping in-time drift cell hits identified as being associated with a track of a particular charged particle passing through said detector;
(c) initially estimating time zero for said particular charged particle;
(d) determining drift radii based on estimates of time zero, drift time conversion data and the time of the hit;
(e) fitting linear tracks to drift radii corresponding to a particular time-zero; and
(f) searching and selecting a time-zero value associated with the best of the track fits performed for particular charged particle and computing error in time-zero and tracking parameters.

22. The computer program of claim 21, wherein initially estimating time zero for said particular charged particle comprises
initially estimating time zero for said particular charged particle from said grouped hits.

23. The computer program of claim 21, wherein determining drift radii based on estimates of time zero, drift time conversion data and the time of the hit comprises
subtracting each hit time of the grouped hits from said initial estimate of time zero to determine each drift time of each hit;
converting said drift times to radii based on predetermined experimental/theoretical drift time to drift distance data stored in a database.

24. The computer program of claim 21, wherein fitting linear tracks to drift radii corresponding to a particular time-zero includes
fitting linear tracks of charged particles passing through first and second sets of drift cells, respectively, using obtained drift radii;
wherein searching and selecting a time-zero value associated with the best of the track fits performed for particular charged particle and computing error in time-zero and tracking parameters comprises
determining a minimum value of chi-square based on track fits for first and second sets of drift cells and said drift radii;
adding together chi-squares for fitted tracks to determine total chi-square;
storing chi-square value for each estimate of value of time-zero;
performing a search to determine time-zero corresponding to the lowest estimated value of chi-square; and
determining a parabolic fit to at least three lowest points to determine error of time-zero selection; and
determine linear track using correct time-zero selection.

* * * * *